(12) United States Patent
Twardowski

(10) Patent No.: US 6,423,050 B1
(45) Date of Patent: Jul. 23, 2002

(54) METHOD AND APPARATUS FOR LOCKING OF CENTRAL-VEIN CATHETERS

(76) Inventor: Zbylut J. Twardowski, 304 Devine Ct., Columbia, MS (US) 65203

( * ) Notice: Subject to any disclaimer, the term of this patent is extended or adjusted under 35 U.S.C. 154(b) by 0 days.

(21) Appl. No.: 09/595,611

(22) Filed: Jun. 16, 2000

(51) Int. Cl.[7] .............................................. A61M 31/00
(52) U.S. Cl. ....................... 604/500; 604/181; 604/191; 604/93.01; 604/167.01; 604/523
(58) Field of Search ................................ 604/181, 187, 604/72, 68, 218, 235, 82, 90, 91, 199, 191, 264, 266, 269, 500, 36, 38, 47, 508, 890.1, 93.01, 173, 288.01–288.04, 523, 81, 80, 158, 163, 164.01, 164.08, 167.01, 167.06, 170.01; 222/129, 132, 135–138, 142.5, 142.9, 386; 514/21, 822; 424/529, 532, 409, 405; 128/DIG. 12, DIG. 18

(56) References Cited

U.S. PATENT DOCUMENTS

| | | | |
|---|---|---|---|
| 4,604,093 A | * | 8/1986 | Brown et al. ................ 604/248 |
| 4,687,475 A | * | 8/1987 | Tai et al. ..................... 604/248 |
| 4,832,682 A | * | 5/1989 | Sarnoff ......................... 604/21 |
| 4,925,444 A | * | 5/1990 | Orkin et al. .................... 604/80 |
| 4,929,230 A | | 5/1990 | Pfleger |
| 4,929,424 A | * | 5/1990 | Desecki et al. ............. 604/266 |
| 5,026,353 A | | 6/1991 | Bartman |
| 5,122,117 A | | 6/1992 | Haber et al. |
| 5,240,146 A | * | 8/1993 | Smedley et al. ............. 222/137 |

(List continued on next page.)

OTHER PUBLICATIONS

Seddon PA, et al. Effectiveness of Low Dose Urokinase on Dialysis Thrombolysis. ASAIO Journal 44:M559–61, 1998.
Twardowski ZJ. High–dose Intradialytic Urokinase to Restore the Patency of Permanent Central Vein Hemodialysis Catheters. Am J Kidney Dis 31:841–7, 1998.
Schwab SJ, et al. The hemodialysis catheter conundrum: Hate living with them, but can't live without them. Kidney Int 56: 1–17, 1999.

(List continued on next page.)

Primary Examiner—Brian L. Casler
Assistant Examiner—Cris L. Rodriguez
(74) Attorney, Agent, or Firm—Seyfarth Shaw

(57) ABSTRACT

A central-vein cathether is locked by anticoagulant and bactericidal solutions separated by an air bubble. The anticoagulant is injected first, then the air bubble, and then the bactericidal solution, so that the anticoagulant is located close to the catheter tip in contact with the blood and the bacterial solution is located close to the catheter hub, where bacteria contamination is common. The air bubble prevents mixing of the solutions. A multi-chamber syringe facilitates sequential injection of the anticoagulant, air and bactericidal agent with only one connection, decreasing chances of contamination. The syringe includes internal and external coaxial barrels separated by seals, the external barrel having a discharge opening located off center in the barrel bottom, and the internal barrel having two or three chambers, each with an outlet opening. The internal barrel is rotatable relative to the external barrel to consecutively align the outlet openings with the discharge opening, allowing sequential injection of the contents. The syringe may also be used for aspiration of the locking fluid from the catheter with only one connection.

17 Claims, 5 Drawing Sheets

U.S. PATENT DOCUMENTS

| | | | | |
|---|---|---|---|---|
| 5,429,276 A | * | 7/1995 | Esclar et al. | 222/136 |
| 5,433,705 A | * | 7/1995 | Giebel et al. | 604/82 |
| 5,549,569 A | * | 8/1996 | Lynn et al. | 604/191 |
| 5,647,856 A | | 7/1997 | Eykmann et al. | |
| 5,688,252 A | | 11/1997 | Matsuda et al. | |
| 5,688,516 A | * | 11/1997 | Raad et al. | 424/409 |
| 5,772,630 A | * | 6/1998 | Ljungquist | 604/90 |
| 5,823,961 A | * | 10/1998 | Fields et al. | 600/434 |
| 5,885,254 A | * | 3/1999 | Matyas | 604/174 |
| 5,899,881 A | | 5/1999 | Grimard et al. | |
| 5,941,854 A | | 8/1999 | Bhitiyakul | |
| 5,947,890 A | | 9/1999 | Spencer et al. | |
| 5,968,017 A | | 10/1999 | Lampropoulos et al. | |
| 5,971,953 A | | 10/1999 | Bachynsky | |
| 6,017,318 A | * | 1/2000 | Gauthier et al. | 600/578 |
| 6,024,727 A | | 2/2000 | Thorne et al. | |
| 6,107,280 A | * | 8/2000 | White et al. | 514/12 |
| 6,166,007 A | * | 12/2000 | Sodemann | 514/222.5 |
| 2001/0003746 A1 | * | 6/2001 | Sodemann | 514/222.5 |
| 2002/0010438 A1 | * | 1/2002 | Finch et al. | 604/265 |

OTHER PUBLICATIONS

Lund GB, et al. Outcome of Tunneled Hemodialysis Catheters Placed by Radiologists. Radiology 198:467–472, 1996.

Beathard GA. Management of Bacteremia Associated with Tunneled–Cuffed Hemodialysis Catheters. J Am Soc Nephrol 10:1045–1049, 1999.

Atkinson JB, et al. Investigational Use of Tissue Plasminogen Activator (t–PA) for Occluded Central Venous Catheters, JPEN J Parenteral Enteral Nutr 14: 310–1, 1990.

Haire WD, et al. Urokinase versus Recombinant Tissue Plasminogen Activator in Thrombosed Central Venous Catheters: A Double–Blinded, Randomized Trial. Thromb Haemost 72:543–7, 1994.

Sodemann K, et al. Gentamicin/sodium–citrate mixture as antibiotic–lock technique for salvage and prevention of catheter–related infections—A four year trial. J Am Soc Nephrol 8:173A, 1997.

* cited by examiner

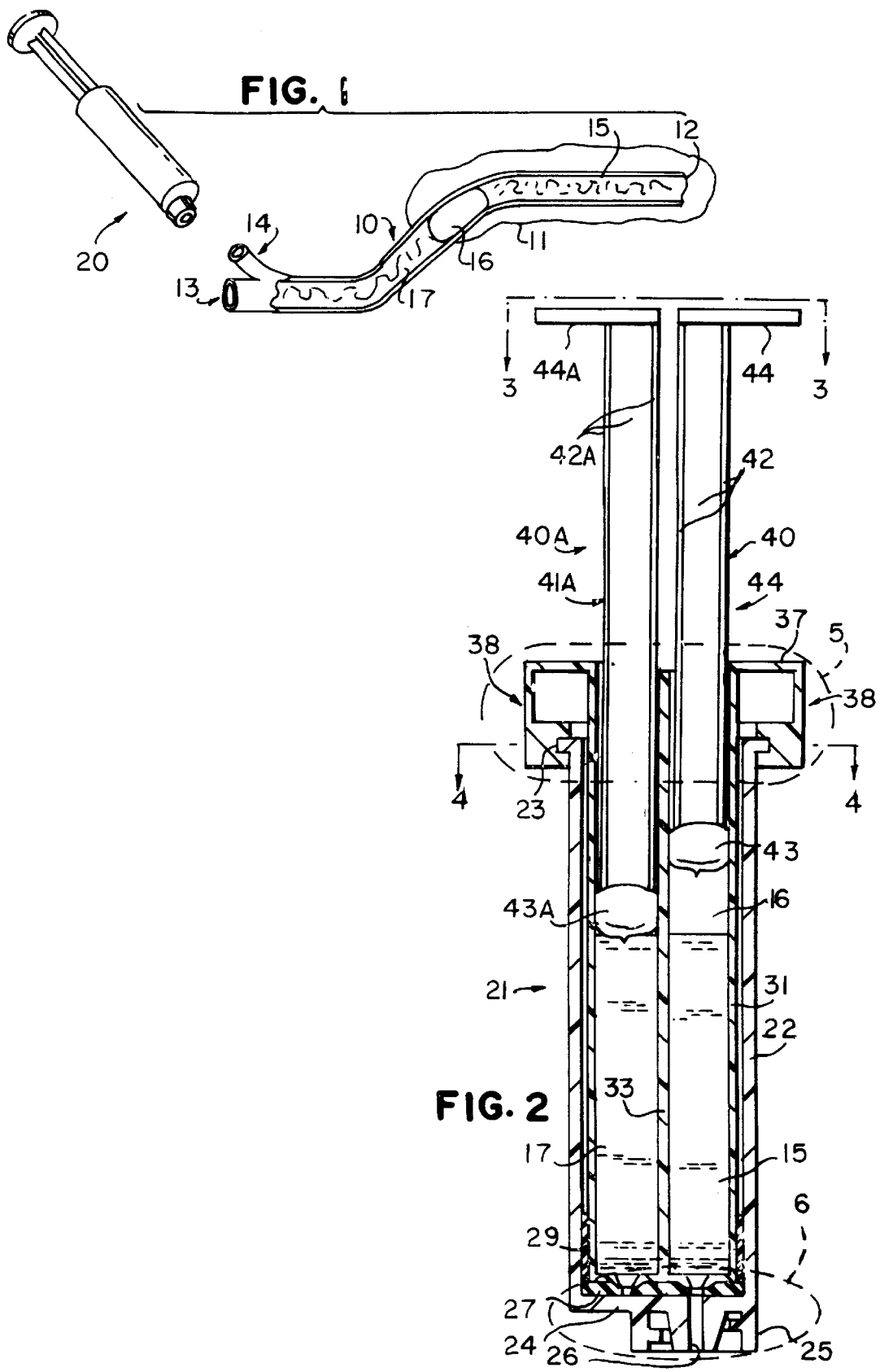

METHOD AND APPARATUS FOR LOCKING OF CENTRAL-VEIN CATHETERS

BACKGROUND

This invention relates to implanted intravenous catheters and, in particular, to techniques for locking such catheters between uses and for prevention of infection.

Intravenous catheters are increasingly used as blood accesses for hemodialysis, plasmapheresis, and for infusion of drugs and nutrients. There are two major complications of intravenous catheters: thrombosis and infection. Both are at least partly related to the method of locking the catheter lumen in periods between uses.

Catheter Locking

Soft, cuffed, single or dual-lumen, central-vein catheters are commonly used as permanent blood accesses. Between uses they are locked by being filled with a fluid to isolate the patient's vascular system from the environment. To prevent clotting, the entire lumen or lumens of such catheters, from hub to tip, are commonly filled with an anticoagulant in the period between uses. This locking solution is aspirated prior to the next use with a syringe and discarded. If the solution cannot be aspirated, because the catheter lumen is clotted, the solution is pushed into the venous system. Such injection of the locking solution may cause excessive anticoagulation or other side effects.

Heparin is the most commonly used anticoagulant to lock catheters between uses. Each lumen is locked with 5,000 to 10,000 units of heparin after dialysis. This solution must be withdrawn from the catheter before the next use, since this much heparin may result in bleeding if infused into the patient. Heparin exerts its anticoagulant activity mainly through activation of Anti-Thrombin III, and it is effective in concentrations as low as 1 unit per ml of blood. Heparin has no ability to lyse preformed thrombi or fibrin sheaths and has no antibacterial properties. In fact, it may promote growth of bacteria within the "biofilm" layer of protein on catheter surfaces. Also, heparin induces severe loss of platelets and paradoxical clotting in some patients (the "white clot" syndrome).

Another anticoagulant used for catheter locking is urokinase, which is derived from urine and kidney cells. It is a serine protease composed of two chains joined by a disulfide bridge. The precursor molecule, single-chain urokinase (scu-PA) is also active. Urokinase is inhibited by plasminogen activator inhibitors 1 and 2, and protease nexin-1. A receptor for urokinase on endothelial cells (u-PAR) may modulate urokinase activity by removal of urokinase-plasminogen activator-inhibitor complexes. Both two-chain and single-chain urokinases are more active in the presence of fibrin and heparin. Catheter lumens maybe locked with urokinase to restore the patency of a clotted catheter, or urokinase may be used instead of heparin to prevent clot formation between dialyses. In case of inability to aspirate the locking solution, the injection of 10,000 units of urokinase is harmless, since much higher doses are used systemically to lyse fibrin sheaths formed on the outer surface of the catheter.

Another anticoagulant used for catheter locking is tissue plasminogen activator, which is a single-chain serine protease with a molecular weight of 68 Kda. Tissue plasminogen activator has not been used for routine locking of catheters, but has been used in small doses (1–2 mg) to restore patency of clotted catheter lumens. Injection of this small dose of tissue plasminogen activator present in the catheter lumen has no systemic effect.

Catheter Infections

Infection associated with catheters is a major reason for their removal. The major source of infection in cuffed catheters appears to be contamination of the catheter hub or lumen during connection or disconnection procedures at the start of and completion of hemodialysis. Periluminal migration of bacteria along the external surface of the catheter as a source of infection seems to be less common, since most catheter-associated bacteremias are not combined with exit or tunnel infection. The surfaces of catheters create a conducive environment at which bacteria can grow and impede phagocytosis by white blood cells. Furthermore, the bacteria can produce a biofilm, i.e., a coating of proteins and glycocalyx that protects bacteria from antibiotics and white cells.

None of the aforementioned anticoagulant locking solutions has any significant antibacterial properties and, therefore, none is of any assistance in combating or preventing infection. While it is possible to lock catheters with bactericidal agents, such as concentrated (27%) sodium chloride, 10% povidone iodine, 4% chlorhexidine, or 1% sodium hypochlorite, none of these bactericidal agents has any anticoagulant activity.

If systemic antibiotics are used for treating bacteremia, they will have an antibiotic action while they are present in the catheter, but this occurs only when blood is flowing through the catheter lumen, such as in dialysis. Treatment with systemic antibiotics is frequently ineffective and removal of the catheter becomes necessary, due to persistent bacteremia (caused by catheter colonization) or worsening clinical condition, Catheter removal, however, is not always possible due to the difficulty in creating alternative blood access. Infection also is the major reason for removal of the smaller cuffed central venous catheters used for infusion of drugs or total parenteral nutrition. Their internal surfaces may also be subjected to antibiotic agents, but only during antibiotic infusion.

One approach to salvaging a colonized catheter is the use of flush solutions, i.e., to lock the ports of the catheter with a mixture of an antibiotic and an anticoagulant or thrombolytic agent. The disadvantage of this method is the diffusion of small amounts of antibiotic into the systemic circulation. This may cause induction of resistant organisms, a growing concern for all antibiotics. For this reason, it is unlikely that the Food and Drug Administration (FDA) would approve chronic catheter locking with antibiotics, and the use of antibiotics for infection prophylaxis should be avoided.

Another approach is to use as a locking solution trisodium citrate, which may have both anticoagulant and antibacterial properties. However, while studies have indicated that concentrated trisodium citrate is able to kill or prevent the growth of most bacteria, it seems to have only a weak effect on staphylococcus aureus, which, of the most common microorganisms responsible for catheter-associated infections, is the most virulent and difficult to eradicate without catheter removal. Another disadvantage of catheter locking with concentrated citrate trisodium is its ability to induce transient hypocalcemia, tingling of the fingers and metallic taste when injected into the bloodstream even in small amounts. Even transient hypocalcemia may cause arrhythmia.

It would be possible to inject an anticoagulant agent into the catheter, followed by injection of a non-antibiotic bactericidal agent. However, diffusion would cause mutual dilution of both the anticoagulant agent and the bactericidal agent. Dilution of the anticoagulant should be avoided in order to prevent clot formation at the tip of the catheter.

Also, diffusion of the solutions increases the risk of strong bactericidal agents being brought into contact with the blood, a condition which should also be avoided.

SUMMARY

As mentioned above, most data indicate that contamination of the catheter hub is the most common etiology of catheter-associated bacteremia. For prevention of intraluminal clot formation it is important to maintain the presence of an anticoagulant at the catheter tip. Thus, ideally, for antibacterial action, the catheter lumen should be filled with bactericidal solution in the external or proximal portion of the lumen (close to the hub), and for prevention of clotting should be filled with anticoagulant solution in the internal or distal part of the lumen (close to the tip). However, for the reasons explained above, the solutions should not mix.

Accordingly, a fundamental aspect of the invention is the locking of a catheter by the use of an anticoagulant agent and an antimicrobial agent with a separator therebetween. More specifically, the invention utilizes an air bubble to separate the anticoagulant and antimicrobial agents.

Another aspect of the invention is the use of a multi-chamber syringe for injection of the locking material into the catheter.

A further aspect of the invention is the use of such a multi-chamber syringe for aspiration of the locking material from the catheter.

A still further aspect of the invention is the provision of a unique multi-chamber syringe suitable for these purposes.

Certain ones of these and other aspects of the invention may be realized by providing a method of preserving the operative condition of an implanted vascular access catheter having inner and outer ends, between uses of gaining access to the vascular system of the patient, the method comprising: inserting an anticoagulant agent through the catheter outer end to drive any blood in the catheter back into the patient vascular system and to fill an inner portion of the catheter with the anticoagulant agent; then inserting a separating substance into the catheter to fill a central portion of the catheter; and then inserting an antimicrobial agent into the catheter to fill an outer portion of the catheter, whereby the separating substance separates the anticoagulant agent from the antimicrobial agent.

Other aspects of the invention maybe realized by providing a syringe comprising an external barrel having an end seal with a discharge opening therein and an internal barrel disposed within the external barrel and having plural separated chambers each having an outlet opening and a plunger, the internal barrel being movable relative to the external barrel among a closed condition wherein the outlet openings are in sealing engagement with the seal and plural injection conditions wherein the outlet openings are respectively disposed in communication with the discharge opening.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

FIG. 1 is a perspective fragmentary view of a catheter implanted in the intravenous system of a patient and locked in accordance with the invention;

FIG. 2 is a longitudinal sectional view of a two-chamber syringe in accordance with one embodiment of the invention;

Detailed Description

Figure 3:
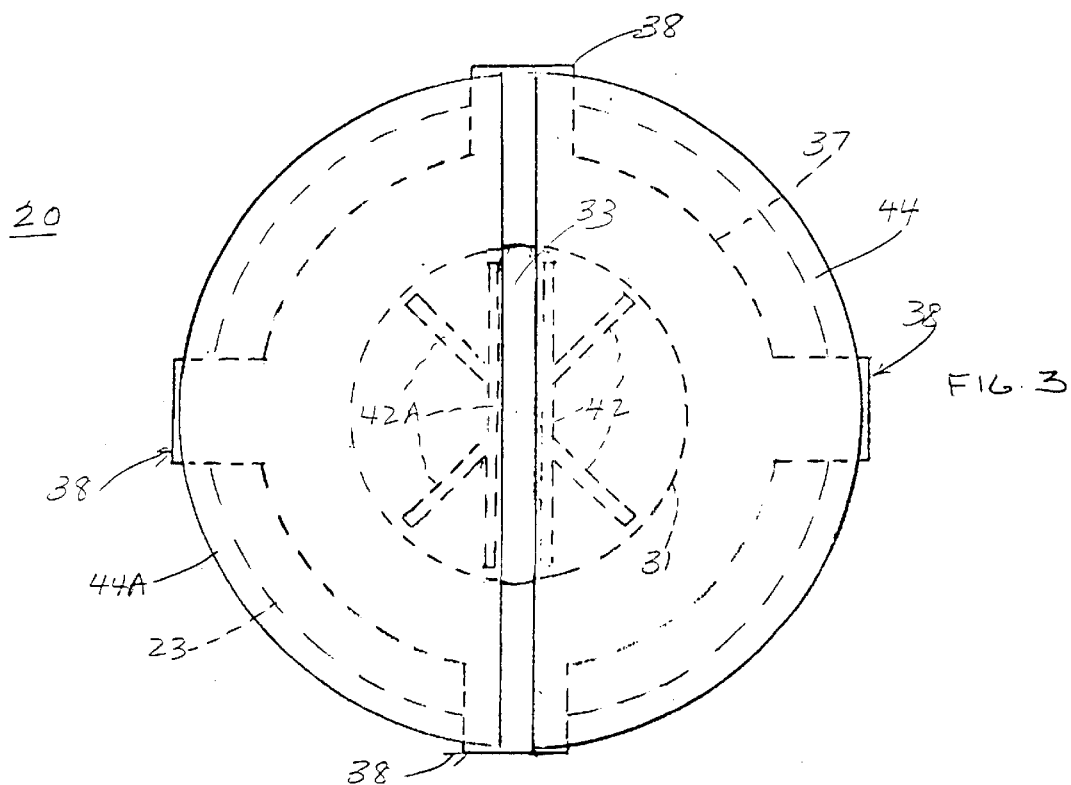
FIG. 3 is an enlarged top plan view of the two-chamber syringe of FIG. 2.
Figure 4:
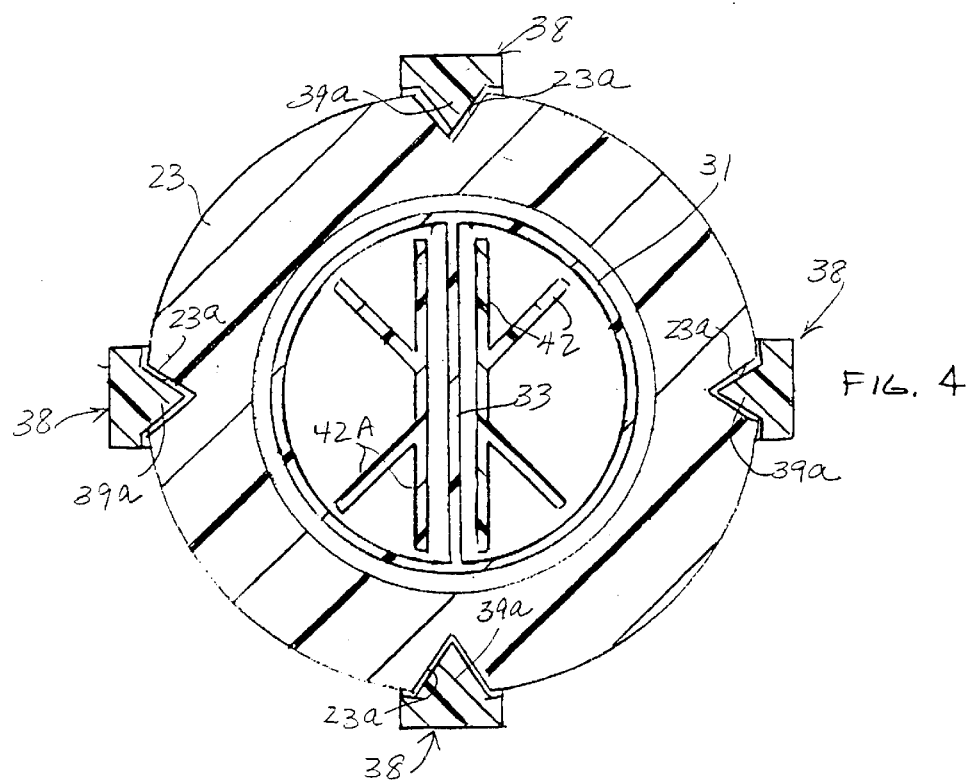
FIG. 4 is an enlarged sectional view taken generally along the line 4—4 in FIG. 2.
Figure 5:
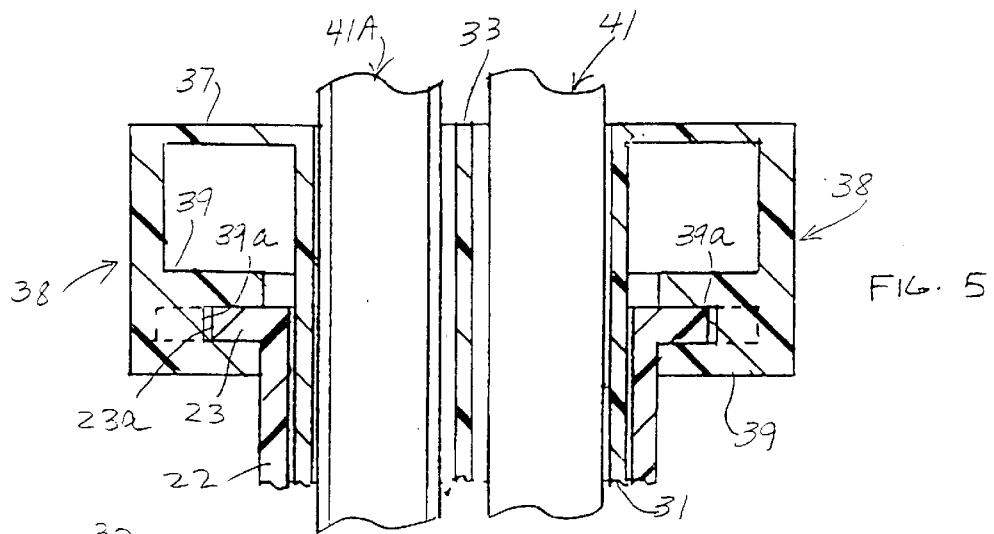
FIG. 5 is an enlarged fragmentary view of a portion of FIG. 2.

Referring to FIG. 1, there is illustrated a catheter 10 implanted in a vein 11 of a patient, the catheter having a distal or inner end or tip 12 disposed in the vein 11 and a proximal or outer end or hub 13, disposed outside the patient's body. Also illustrated is a two-chamber syringe 20 in accordance with the invention, the details of which will be explained more fully below, which may be used in performing the method of the invention. The hub has a Y-connector 14 adapted for connection to a conduit set of associated apparatus, such as for performing dialysis or the like, in a known manner. When not in use, the catheter 10 is filled with a locking fluid and the Y-connector 14 is then closed off with a suitable closure. The present invention relates to a method and apparatus for effecting the catheter lock.

The lumen of the catheter 10 has a specific capacity provided by the manufacturer. To fill the entire catheter lumen, a measured volume of fluid will be used. In accordance with the method of the invention, approximately one-half of the lumen capacity will be injected with a solution of an anticoagulant agent 15 driving any blood in the catheter back into the patient's vascular system. Then, a separating substance, such as a small air bubble 16, which may be about 0.1 ml in volume, will be injected, followed by injection of an antimicrobial agent 17, such as a bactericidal solution of calculated volume to fill the remainder of the catheter lumen. Then the catheter is closed. In vitro experiments have shown that two solutions separated by an air bubble do not mix if left in glass tubes and agitated catheters for several weeks. Thus, the air bubble 16 is effective to maintain the presence of the anticoagulant agent 15 at the catheter tip, while maintaining the antimicrobial agent 17 in the outer portion of the catheter lumen, without fear of the two solutions mixing. Prior to the next catheter use, the locking substances are aspirated and the dialysis or infusion is started in a routine manner.

In current practice, in case of catheter blockage by a clot, frequently the locking solution cannot be aspirated and is, therefore, injected into the patient. As mentioned above, excessive anticoagulation or other side effects may result from such injection. The injection of bactericidal solution may cause even more severe side effects and, therefore, it is essential to aspirate bactericidal solution from the catheter lumen. In vitro experiments using the method of the invention, show that the bactericidal solution can be readily aspirated in clamped catheters, since the air bubble 16 readily expands at negative pressure. Once the bactericidal solution is aspirated, the external catheter lumen is clamped, a saline-filled syringe is attached and the saline injected and aspirated again. This maneuver may be repeated, as needed, to insure complete removal of the bactericidal solution.

Because many bactericidal agents if injected into a patient may have adverse affects, a preferred bactericidal solution may be acidified concentrated saline, specifically 27% NaCl acidified with HCl to a pH of 2.0. To achieve a pH of 2.0, 1 mL of concentrated (37%) HCl may be added to 1 L of concentrated (27%) NaCl, whereby 1 mL of bactericidal solution will contain 270 mg of NaCl and 0.37 mg of HCl. Such an acidified concentrated saline solution would have no adverse effects if injected into a patient.

Figure 6:
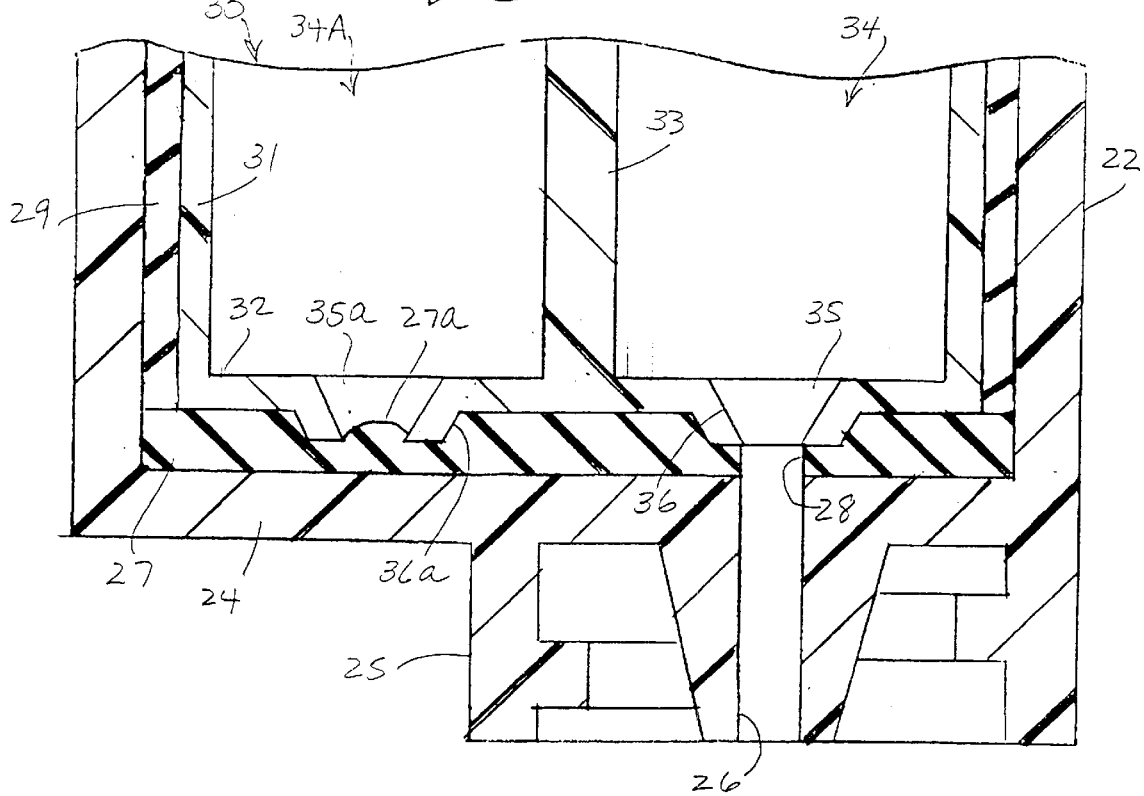
FIG. 6 is an enlarged fragmentary view of the lower end of FIG. 2.

While the locking substances may be injected into the catheter 10 by the use of any desired means, in one form of the invention the injection is effected by the use of a specially-designed multiple-chamber syringe, one such syringe being illustrated in FIGS. 2–6. The use of this syringe permits the locking solutions to be added with only a single connection to the catheter, which significantly decreases the chances of catheter infection. Referring to FIGS. 2–6, there is illustrated the two-chamber syringe 20 which has an external barrel 21 with an elongated cylindrical body 22, provided at one end thereof with a radially outwardly projecting annular flange 23 having four equiangularly spaced notches 23a formed therein (see FIG. 4). The other end of the body 22 is closed by an end wall 24 which carries a Luer-lock tip 25, which defines a discharge port 26. The inner surface of the end wall 24 is covered with a seal 27 having a discharge opening 28 therethrough communicating with the discharge port 26 (FIG. 6).

The syringe 20 also includes an internal barrel 30 having a cylindrical outer wall 31 disposed coaxially within the external barrel 21 and in sealing engagement with the seal 29. The inner end of the cylindrical outer wall 31 is closed by an end wall 32. A diametrical septum 33 extends across the outer wall 31 along its entire length and divides it into two chambers 34 and 34A. Formed in the end wall 32 are two outlet openings 35 and 35A, respectively communicating with the chambers 34 and 34A, and respectively provided with tips 36 and 36A disposed in sealing engagement with the seal 27 (FIG. 6). A peripheral seal 29 is disposed along the outer surface of the lower end of the outer wall 31 and in sealing contact with the body 22 and with the seal 27. The outer wall 31 is slightly longer than the external barrel 21 and projects upwardly therefrom. Integral with the outer wall 31 at its other end and extending radially outwardly therefrom is an annular flange 37 provided with four equiangularly spaced depending clips 38. Each clip 38 has at its lower end a shoe 39 with a radially inwardly projecting tooth 39a dimensioned and positioned for engagement in a corresponding one of the notches 23a in the external barrel flange 23, as can best be seen in FIGS. 4 and 5. The notches 23a and the teeth 39a may be generally V-shaped in transverse cross section so as to define slopping cam surfaces. The clips 38 have sufficient flexibility and resilience that the teeth 39a can be cammed out of the notches 23a to permit rotation of the internal barrel 30 relative to the external barrel 21.

The chambers 34 and 34A are respectively provided with plungers 40, 40A, which may be substantially identical in construction. The plungers 40,40A respectively have elongated bodies 41, 41A made up of a plurality of interconnected flange walls 42, 42A. The bodies are respectively provided at their inner ends with gaskets 43, 43A and at their outer ends with handles 44, 44A.

The Luer-lock tip 25 is disposed eccentrically of the external barrel end wall 24, and the outlet openings 35 and 35A of the chambers 34, 34A are respectively positioned so that they can be brought into communication with the discharge port 26 by rotation of the internal barrel 30. Before use, the internal barrel 30 is disposed in a closed or "neutral" position wherein neither outlet opening 35, 35A is disposed in communication with the discharge port 26, and both are sealed by the seal 27 and, more specifically, by tiny bulges 27a of the seal 27 which project upwardly slightly into the tip 36, 36A (see FIG. 6). The chamber 34 is partially filled with a predetermined volume of an anticoagulant agent 15, and a small volume, e.g., 0.1–0.2 ml, of air 16. The chamber 34A is filled with an antimicrobial agent 17, such as a bactericidal solution. The Luer-lock tip 25 is then connected to the catheter 10 in a known manner and the internal barrel is rotated 90° so as to bring the outlet opening of the anticoagulant chamber 34 into alignment with the discharge port 26 and the discharge opening 28. In this position, the teeth 39a of the clips 38 will again be engaged in the notches 23a, serving as detents to prevent accidental movement of the internal barrel 30 from the selected position. The anticoagulant agent 15 and the airbubble 16 are then injected into the catheter 10. Then, the internal barrel 30 is rotated 180° to bring the outlet opening of the other chamber 34A into alignment with the discharge port 26, whereupon the bactericidal agent is injected into the catheter 10. The syringe 20 may then be disconnected from the catheter 10, which may then be closed.

As was indicated above, the syringe 20 could also be used for aspiration of the locking fluids before the next use of the catheter 10. Thus, for this purpose the syringe 20 would be connected to the catheter 10 as before, then the chamber 34A would be rotated into alignment with the discharge port 26 for aspiration of the bactericidal solution 17, the air bubble 16 simply expanding as the pressure is reduced. Then the internal barrel 30 would be rotated to bring the other chamber 34 into alignment with the discharge port for aspiration of the air bubble 16 and the anticoagulant agent 15, whereupon the internal barrel 30 would be rotated to the closed or neutral position.

Figure 7:
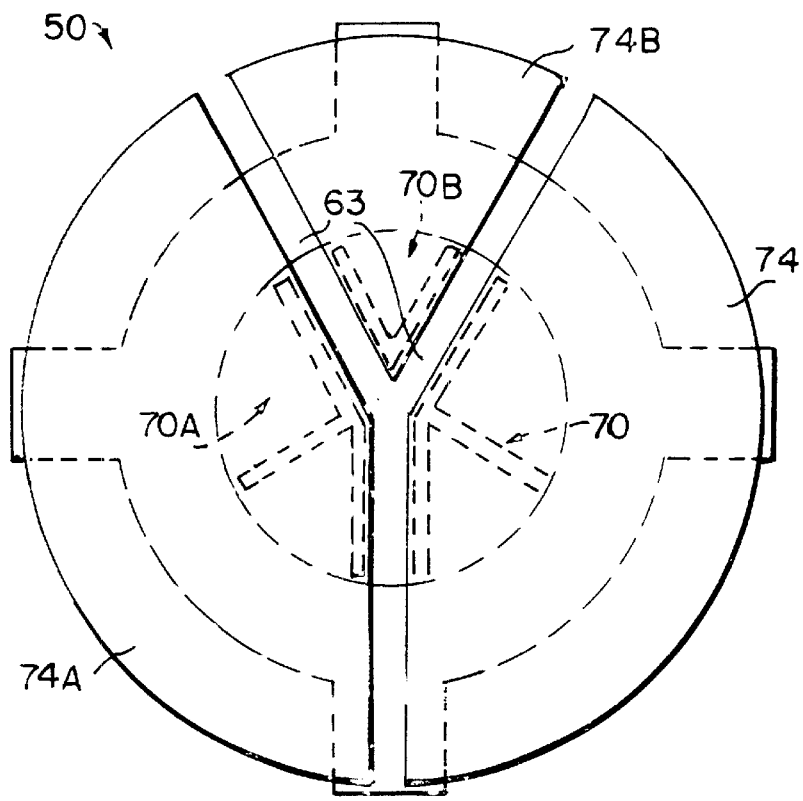
FIG. 7 is a view similar to FIG. 3 of another embodiment of the invention.
Figure 8:
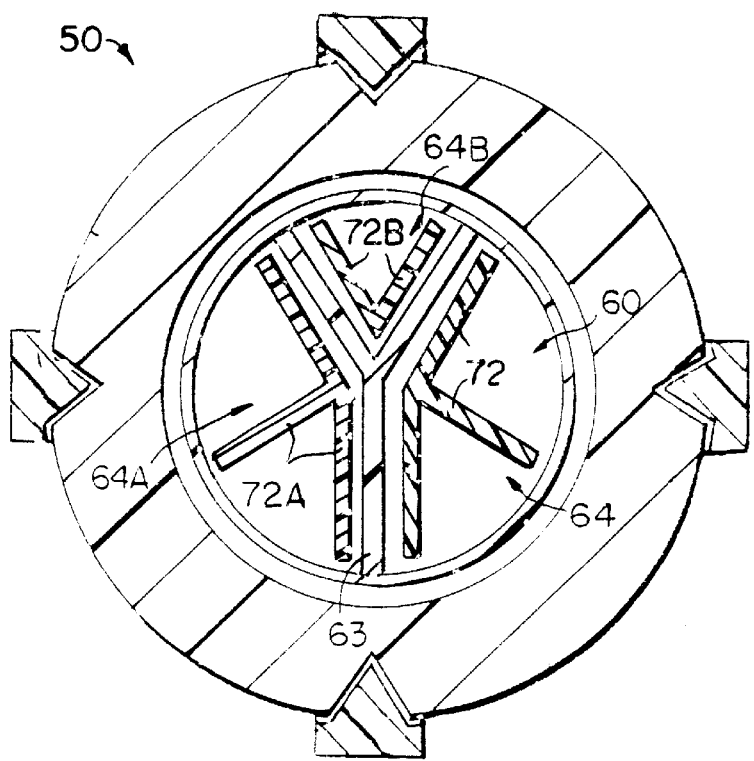
FIG. 8 is a top plan view similar to FIG. 4 of the embodiment of FIG. 7.
Figure 9:
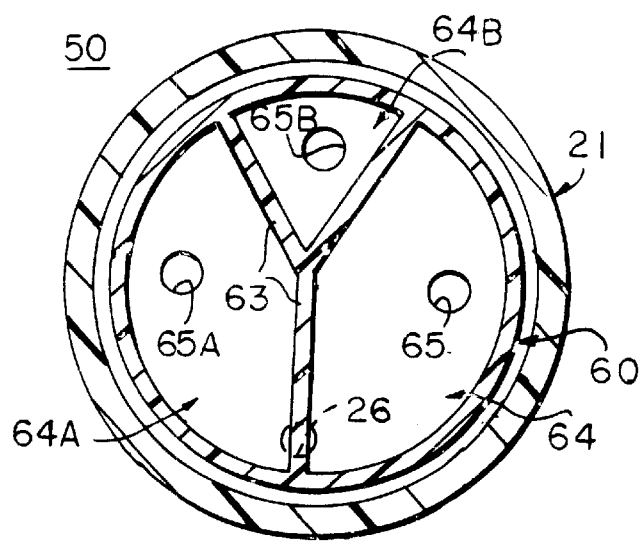
FIG. 9 is a cross sectional view of the syringe of FIG. 8 just above the bottom of the internal barrel.

Referring to FIGS. 7–9, there is illustrated a three-chamber syringe 50 in accordance with another embodiment of the invention. The syringe 50 has an external barrel which may be substantially identical to external barrel 21, described above, and an internal barrel 60 disposed coaxially within the external barrel 21. The internal barrel 60 is similar to the internal barrel 30, described above, and like parts bear the same reference numerals. The basic difference is that the internal barrel 60 has a Y-shaped septum 63 which divides the outer wall 31 into three chambers 64, 64A, and 64B, respectively having outlet openings 65, 65A, and 65B. The chambers 64 and 64A are substantially the same size and shape and are much larger than the chamber 64B. The chambers 64,64A, and 64B are respectively provided with similarly-shaped plungers 70, 70A, and 70B, which respectively have bodies made up of interconnected flange walls 72, 72A, and 72B, and respectively provided with gaskets (not shown) at their inner ends and handles 74, 74A, and 74B at their outer ends.

The syringe 50 has a neutral position wherein all of the outlet openings 65, 65A, and 65B are sealed, as illustrated in FIG. 9. The chambers 64, 64A, and 64B are, respectively, filled with anticoagulant, bactericidal solution and air, and they are respectively moved into alignment with the outlet port 26 for sequential injection of these locking fluids into the catheter 10. The syringe 50 may also be used for aspiration of the locking fluids from the catheter.

Figure 10:
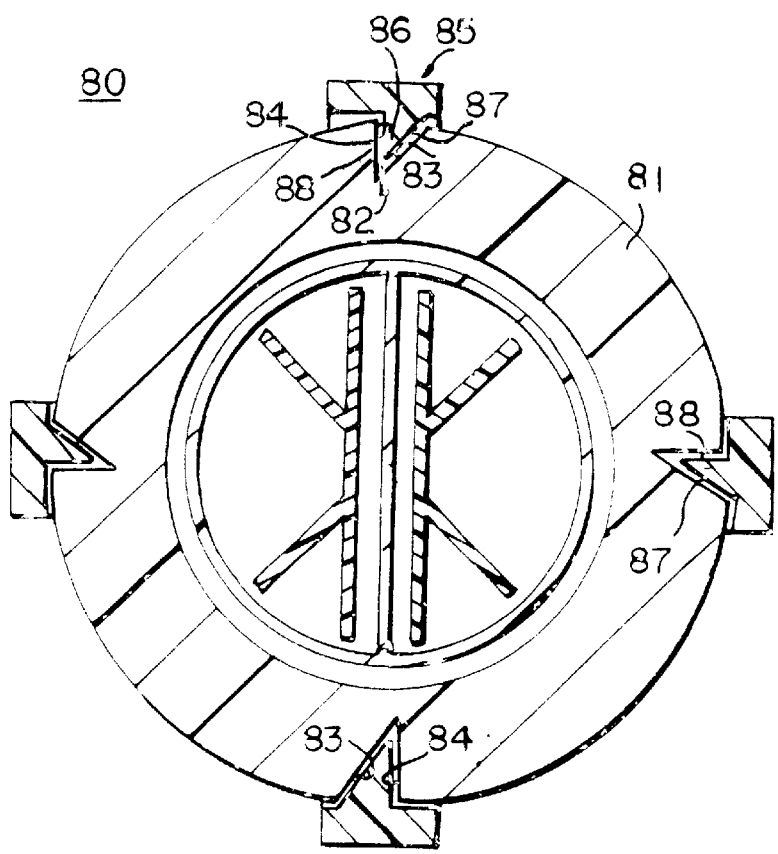
FIG. 10 is a view similar to FIG. 4, showing an alternative embodiment.

Referring to FIG. 10, there is illustrated a portion of an alternative syringe 80 which is similar to the syringe 20, described above, except for the changes described below. The syringe 80 has an external barrel with a flange 81 which corresponds to the flange 23 of the syringe 20, except that it is provided with notches 82 which, instead of being in the form of isosceles triangles, are in the from of right triangles, each having a non-radial cam surface 83 and a substantially radial stop surface 84. The syringe 80 also has an internal barrel similar to the internal barrel 30, except that it is provided with clips 85 respectively having teeth 86 shaped and dimensioned for mating engagement in the notches 82. Thus, each tooth 86 has a cam surface 87 and a stop surface 88. It will be appreciated that the shape of the notches 82 and the teeth 86 will permit rotation of the internal barrel in a clockwise direction, as viewed in FIG. 10, but will prevent rotation in a counterclockwise direction. With this embodiment, the contents of the chambers of the internal barrel can be arranged so as to be sequentially brought into position for proper sequential injection into the catheter when the internal barrel is rotated clockwise. The arrangement prevents counterclockwise rotation and, thereby, inhibits injection of the locking fluids in an incorrect order. It will be appreciated that a similar arrangement could be used with the three-chamber syringe 50.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicant's contribution. The actual scope of the protection sought is intended to be defined in the following claims when viewed in their proper perspective based on the prior art.

I claim:

1. A method of preserving the operative condition of an implanted vascular access catheter having inner and outer ends, between the uses of gaining access to the vascular system of a patient, the method of comprising:

inserting an anticoagulant agent through the catheter outer end to drive any blood in the catheter back into the patient vascular system and to fill an inner portion of the catheter with the anticoagulant agent;

then inserting a seperating substance into the catheter to fill a central portion of the catheter; and then inserting an antimicrobial agent into the catheter to fill an outer portion of the catheter, the preceding insertion steps being performed without discharging the agents or the substance from the inner end of the catheter, whereby the separating substance separates the anticoagulant agent from the antimicrobial agent.

2. The method of claim 1, which comprises the subsequent step of closing off the catheter outer end.

3. The method of claim 1, wherein each of the agents is a liquid.

4. The method of claim 3, wherein the separating portion is a gas.

5. The method of claim 4, wherein the gas is air.

6. The method of claim 1, wherein the separating portion is a gas.

7. The method of claim 6, wherein the gas is air.

8. The method of claim 1, wherein the antimicrobial agent is a bactericidal agent.

9. The method of claim 8, wherein the bactericidal agent is acidified concentrated saline solution.

10. The method of claim 1, wherein the agents and the separating substance are sequentially inserted into the catheter using a multiple-chamber syringe.

11. A method of preserving the operative condition of an implanted vascular access catheter having inner and outer ends, between uses of gaining access to the vascular system of a patient, the method comprising:

providing a syringe having plural separated chambers each having an outlet opening and a plunger and movable among injection conditions wherein the outlet openings respectively communicate with a discharge opening, filling the chambers respectively with plural locking fluids, connecting the discharge opening to the outer end of the catheter, and sequentially injecting the fluids from the chambers into the catheter without discharging the fluids from the inner end of the catheter.

12. The method of claim 11, wherein the locking fluids include an anticoagulant agent and an antimicrobial agent.

13. The method of claim 12, wherein the locking fluids include a separating substance.

14. The method of claim 13, wherein the syringe has two chambers.

15. The method of claim 13, wherein the syringe has three chambers.

16. The method of claim 13, wherein the separating substance is a gas.

17. The method of claim 16, wherein the gas is air.

* * * * *